US012807568B2

(12) United States Patent
Lee et al.

(10) Patent No.: US 12,807,568 B2
(45) Date of Patent: Nov. 24, 2026

(54) THIOL-BASED BETA-DIKETONE PRIMERS FOR ADHESION TO METAL

(71) Applicant: 3M INNOVATIVE PROPERTIES COMPANY, St. Paul, MN (US)

(72) Inventors: Hae-Seung Harry Lee, Woodbury, MN (US); Steven R. Austin, Oakdale, MN (US); Matthew J. Kryger, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 125 days.

(21) Appl. No.: 18/683,434

(22) PCT Filed: Aug. 19, 2022

(86) PCT No.: PCT/IB2022/057798
§ 371 (c)(1),
(2) Date: Feb. 13, 2024

(87) PCT Pub. No.: WO2023/042009
PCT Pub. Date: Mar. 23, 2023

(65) Prior Publication Data

US 2025/0136546 A1 May 1, 2025

Related U.S. Application Data

(60) Provisional application No. 63/261,381, filed on Sep. 20, 2021.

(51) Int. Cl.

| | |
|---|---|
| ***C07C 323/52*** | (2006.01) |
| ***B32B 5/18*** | (2006.01) |
| ***B32B 7/14*** | (2006.01) |
| ***B32B 15/04*** | (2006.01) |
| ***B32B 15/20*** | (2006.01) |
| ***C09J 181/02*** | (2006.01) |

(52) U.S. Cl.
CPC .............. *C07C 323/52* (2013.01); *B32B 5/18* (2013.01); *B32B 7/14* (2013.01); *B32B 15/046* (2013.01); *B32B 15/20* (2013.01); *C09J 181/02* (2013.01); *B32B 2255/06* (2013.01); *B32B 2255/26* (2013.01); *B32B 2307/748* (2013.01); *C09J 2301/124* (2020.08); *C09J 2481/00* (2013.01)

(58) Field of Classification Search
None
See application file for complete search history.

(56) References Cited

U.S. PATENT DOCUMENTS

| | | | | |
|---|---|---|---|---|
| 4,303,485 | A | 12/1981 | Levens | |
| 4,329,384 | A | 5/1982 | Vesley et al. | |
| 4,330,590 | A | 5/1982 | Vesley | |
| 4,415,615 | A | 11/1983 | Esmay et al. | |
| 5,288,802 | A | 2/1994 | Walters et al. | |
| 5,804,610 | A | 9/1998 | Hamer et al. | |
| 5,913,970 | A | 6/1999 | Atkins et al. | |
| 6,103,152 | A | 8/2000 | Gehlsen et al. | |
| 6,433,097 | B1 * | 8/2002 | Nixon | C08F 8/00 525/107 |
| 6,521,716 | B1 * | 2/2003 | Leake | C09J 167/06 525/425 |
| 6,586,483 | B2 | 7/2003 | Kolb et al. | |
| 8,298,367 | B2 | 10/2012 | Beger et al. | |
| 8,618,204 | B2 | 12/2013 | Campbell et al. | |
| 2014/0255638 | A1 * | 9/2014 | Imai | C09J 7/387 451/28 |
| 2016/0376448 | A1 * | 12/2016 | Powell | C09D 5/086 427/388.1 |
| 2020/0283647 | A1 * | 9/2020 | Yasuhara | C09D 201/02 |

FOREIGN PATENT DOCUMENTS

| | | | | |
|---|---|---|---|---|
| WO | 2011001419 | A1 | 1/2011 | |
| WO | 2015183782 | A1 | 12/2015 | |
| WO | 2016089805 | A1 | 6/2016 | |
| WO | 2016145359 | A1 | 9/2016 | |
| WO | WO-2019064103 | A1 * | 4/2019 | C08L 81/02 |
| WO | 2019239346 | A1 | 12/2019 | |
| WO | WO-2019239273 | A1 * | 12/2019 | C08G 75/045 |
| WO | 2020217161 | A1 | 10/2020 | |
| WO | 2023012542 | A1 | 2/2023 | |

(Continued)

OTHER PUBLICATIONS

Eastman™ AAEM (acetoacetoxyethyl methacrylate) Acetoacetyl chemistry Technical Report, Eastman Chemical Company, Jan. 2013, pp. 1-10.

Eastman™ Acetoacetoxyethyl Methacrylate as a reactive copromoter/diluent in unsaturated polester resins Technical Report, Eastman Chemical Company, Oct. 2008, pp. 1-7.

International Search Report for PCT International Application No. PCT/IB2022/057798, mailed on Nov. 16, 2022, 5 pages.

Martinez, "The Inhibition of Copper-Nickel Alloy Corrosion Under Controlled Hydrodynamic Condition In Seawater", Journal of Applied Electrochemistry, 2006, vol. 36, pp. 1311-1315.

(Continued)

*Primary Examiner* — John Vincent Lawler

(74) *Attorney, Agent, or Firm* — Ann Benjamin; Lynn R. Hunsberger

(57) ABSTRACT

A primer compound is provided that can be used as an adhesion promoter on various substrates, particularly metal-containing substrates. Articles containing a metal-containing substrate and a primer layer, which includes the primer compound, positioned adjacent to the substrate are also provided. The articles often include an adhesive layer with the primer layer positioned between the metal-containing substrate and the adhesive layer. The primer compound has a diketone group that can form chelates with various metals through coordination chemistry plus a thiol group that can react with components in the adhesive layer.

10 Claims, No Drawings

(56) References Cited

FOREIGN PATENT DOCUMENTS

WO 2023012543 A1 2/2023

OTHER PUBLICATIONS

Mattioni, "Prediction of Glass Transition Temperatures from Monomer and Repeat Unit Structure Using Computational Neural Networks", Journal of Chemical Information and Computer Sciences, Mar. 2002, vol. 42, No. 2, pp. 232-240.
Nesbitt, "Evaluation of β-diketone-containing Polymeric Coupling Agents for Enhancing the Adhesion of Epoxy to Aluminum", The Journal of Adhesion, Jan. 2000, vol. 72, No. 3-4, pp. 245-268.
Utility of Eastman™ AAEM (acetoacetoxyethyl methacrylate) In thermoset coatings Technical Report, Eastman Chemical Company, Dec. 2012, pp. 1-15.

* cited by examiner

THIOL-BASED BETA-DIKETONE PRIMERS FOR ADHESION TO METAL

CROSS REFERENCE TO RELATED APPLICATIONS

This application is a national stage filing under 35 U.S.C. 371 of PCT/IB2022/057798, filed Aug. 19, 2022, which claims the benefit of U.S. Provisional Patent Application No. 63/261,381, filed Sep. 20, 2021, the disclosure of which is incorporated by reference in its/their entirety herein.

BACKGROUND

Various adhesives can be used to bond a first surface to a second surface. To increase the adhesion of the adhesive to one or both surfaces, various adhesion promoters have been used. For example, various adhesion promoters having an epoxide group and a hydrolyzable silyl group have been described in U.S. Pat. No. 8,618,204 (Campbell et al.) and in PCT patent application publications WO 2019/239346 (Lee et al.) and WO 2020/217161 (Lee et al.).

Acetoacetate is known for its ability to form chelates with various metals through coordinate chemistry. Generally, materials with a diketone group ($-(C-O)-CH_2-(C=O)-$) exist in equilibrium with keto-enol tautomers and can readily form acetylacetonate anions upon losing a methylene proton. The acetylacetonate anions have strong affinity to metals. Due to this metal binding ability, researchers have attempted to develop adhesion promoters or primers for metal bonding applications based on this chemistry. Eastman Chemical Company developed and commercialized 2-(methacrylolyloxy)ethyl acetoacetate (CAS #21282-97-3) for use in various (meth)acrylate polymers for improved adhesion to metal substrates. However, further research indicated that copolymers with 2-(methacryloly-loxy)ethyl acetoacetate did not show improved performance with aluminum (see Nesbit et al., The Journal of Adhesion, 2000, Vol 72, pp 245-268).

There is an ongoing interest in increasing the adhesion between the adhesive composition and various surfaces. More specifically, there is an increasing interest in increasing the adhesion of the adhesive composition to inorganic surfaces such as, for example, metallic surfaces.

SUMMARY

A primer compound is provided that can be used as an adhesion promoter on various substrates, particularly metal-containing substrates. Articles containing a metal-containing substrate and a primer layer, which includes the primer compound, positioned adjacent to the substrate are also provided. The articles often include an adhesive layer with the primer layer positioned between the metal-containing substrate and the adhesive layer. The primer compound has a diketone group that can form chelates with various metals through coordination chemistry plus a thiol group that can react with components in the adhesive layer.

In a first aspect, a primer compound is provided that comprises at least one thiol group and at least one diketone group of formula $-(C=O)-CH_2-(C=O)-$. The primer compound is free of an oxirane group.

In a second aspect, an article is provided that includes (1) a first metal-containing substrate and (2) a first primer layer positioned adjacent to the first metal-containing substrate, wherein the first primer layer comprises a first primer compound that comprises at least one thiol group and at least one diketone group of formula $-(C=O)-CH_2-(C=O)-$. The first primer compound, which can form a chelate with a metal in the first metal-containing substrate, is free of an oxirane group. This article can be referred to as a "first article".

In some embodiments of the second aspect, the article (e.g., the first article) further includes at least one adhesive layer positioned adjacent to the first primer layer opposite the first metal-containing substrate. This article, which can be referred to as a "second article", includes multiple layers arranged in the following order: first metal-containing substrate, first primer layer, and at least one adhesive layer. The at least one adhesive layer is typically a pressure-sensitive adhesive. In still other embodiments of the second embodiment, the article yet further includes a second substrate. This article, which can be referred to as a "third article" can have two different constructions. In a first embodiment, the third article includes the second article plus a second primer layer and a second metal-containing substrate. This construction of the third article includes multiple layers arranged in the following order: first metal-containing substrate, first primer layer, at least one adhesive layer, second primer layer, and second metal-containing substrate. In a second embodiment, the third article includes a second substrate that may be a metal-containing substrate or a non-metal containing substrate and an optional primer layer. This construction of the third article includes multiple layers arranged in the following order: first metal-containing substrate, first primer layer, at least one adhesive layer, an optional primer layer, and a second substrate that is a metal-containing substrate or a non-metal containing substrate. The optional primer layer can include no primer compound, a primer compound described herein, or a different type of primer compound.

As used herein, the terms "a", "an", and "the" are all equivalent to "at least one of" and encompass embodiments having plural referents, unless the context clearly dictates otherwise.

The term "or" is generally employed in its sense including "and/or" unless the context clearly dictates otherwise. The term "and/or" such as A and/or B means A alone, B alone, or both A and B.

The term "ethylenically unsaturated group" refers to monovalent group that contains a $CH_2=CR-$ group where R is hydrogen or methyl. The ethylenically unsaturated group is often a vinyl group or the reactive portion of an allyl group of formula $CH_2-CR-CH_2-$ or a (meth)acryloyl group of formula $CH_2-CR-(C-O)-$. (Meth)acryloyl groups are often part of a (meth)acryloyloxy ($CH_2=CR-(C=O)-O-$) or (meth)acryloylimino ($CH_2-CR-(C=O)-NH-$) group.

The term "ene" refers to the monovalent group $CH_2-CR-$ where R is hydrogen or methyl. That is, the ene group can be a vinyl group or the reactive part of an allyl or (meth)acryloyl group.

The term "thiol" refers to a monovalent group $-SH$.

The term "heterohydrocarbon" refers to a compound having heteroatoms such as S, N, or O in addition to carbon and hydrogen.

The term "heterocyclic" refers to a ring structure having a heteroatom ring member such as S, N, or O.

The term "oxirane group" refers to a monovalent group that contains a three membered ring with an oxygen ring member.

The term "diketone group" refers to a divalent group of formula $-(C=O)-CH_2-(C=O)-$. In many embodiments, one of the carbonyl groups is attached to an alkyl such as methyl. This group can be also referred to interchangeably as an "acetoacetate group".

The term "alkyl" refers to a monovalent group that is a radical of an alkane and includes groups that are linear, branched, cyclic, bicyclic, or a combination thereof. Unless otherwise indicated, the alkyl groups typically contain from 1 to 30 carbon atoms but cycloalkyl groups have at least 3 carbon atoms and bicyclic groups typically have at least 6 carbon atoms. In some embodiments, the alkyl groups contain 1 to 20, 1 to 10, 1 to 6, 1 to 4, or 1 to 3 carbon atoms. Example alkyl groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene" refers to a divalent group that is a di-radical of an alkane and includes groups that are linear, branched, cyclic, bicyclic, or a combination thereof. Unless otherwise indicated, the alkylene group typically has 1 to 30 carbon atoms but a cyclic group has at least 3 carbons and a bicyclic group typically has at least 6 carbon atoms. In some embodiments, the alkylene group has 1 to 20 carbon atoms, 1 to 10 carbon atoms, 1 to 6 carbon atoms, 1 to 4 carbon atoms, or 1 to 3 carbon atoms. Example alkylene groups include methylene, ethylene, 1,3-propylene, 1,2-propylene, 1,4-butylene, 1,4-cyclohexylene, and 1,4-cyclohexyldimethylene.

The term "aryl" refers to a monovalent group that is a radical of an aromatic carbocyclic compound. The aryl group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms or 6 to 10 carbon atoms.

The term "aromatic" refers an aromatic group or compound that typically has 3 to 40 carbon atoms or 3 to 30 carbon atoms. The aromatic group or compound can be carbocyclic or can be heterocyclic containing one or more of the heteroatoms (O, N, or S) and typically has at least 5 ring members. The aromatic ring can have one ring or can have multiple fused or attached rings that are each carbocyclic or heterocyclic.

The term "aralkyl" refers to an alkyl group substituted with at least one aryl group. That is, the aralkyl group is of formula —$R^d$—Ar where $R^d$ is an alkylene and Ar is an aryl. The aralkyl group contains 6 to 40 carbon atoms. The aralkyl group often contains an alkylene group having 1 to 20 or 1 to 10 carbon atoms and an aryl group having 5 to 20 or 6 to 10 carbon atoms.

The term "primer compound" refers to a compound having a thiol group plus a diketone group.

The recitation of numerical ranges by endpoints includes the endpoints, all numbers within that range (e.g., 1 to 5 includes 1, 1.5, 2, 2.75, 3, 3.80, 4, and 5), and any range within that range.

DETAILED DESCRIPTION

A primer compound and articles containing at least one layer of the primer compound are provided. The primer compound has 1) at least one diketone group that can form a chelate with a metal in various metal-containing substrates through coordination chemistry and 2) at least one thiol group. An article containing a primer layer comprising the primer compound positioned adjacent to a metal-containing substrate is also provided. The article can optionally further include at least one adhesive layer that is positioned adjacent to the primer layer opposite the metal-containing substrate. Further, the article can still further include two substrates, either one or two primer layers, and at least one adhesive layer arranged in the following order: first metal-containing substrate, first primer layer, at least one adhesive layer, an optional second primer layer, and second substrate that can be either a metal-containing substrate or a non-metal-containing substrate.

When the primer compound is included in a primer layer positioned between a metal-containing substrate and an adhesive composition, the adhesive composition tends to adhere more effectively to the metal-containing substrate. The primer compound is particularly effective for binding to various copper-containing substrates such as copper, brass, and bronze. Additionally, a layer of the primer layer on the metal-containing substrate may advantageously reduce corrosion of the metal-containing substrate, particularly those metal-containing substrates that contain copper, brass, or bronze.

Primer Compound

The primer compound has at least one thiol group and at least one diketone group. The primer compound is a reaction product of a reaction mixture that contains two different types of compounds. The first compound has at least two thiol groups. The second compound contains an ethylenically unsaturated group and a diketone group. The second compound has a terminal ethylenically unsaturated group (i.e., a terminal ene group of formula $CH_2{=}CR^1$— where $R^1$ is hydrogen or methyl) that can react with a thiol group of the first compound. Typically, no other reactive compounds (i.e., a compound that can react with the first compound and/or the second compound) are included in the reaction mixture.

A general reaction scheme to form the primer compound is shown in Reaction Scheme A. Group $Q^1$ in the first compound (1) of formula HS-$Q^1$-HS is the residue of this compound minus the two thiol groups. Although the first compound is shown in Reaction Scheme A as having two thiol groups, it may have more thiol groups. The group $Q^2$ in second compound (2) of formula $CH_2{=}CH$-$Q^2$-(C═O)—$CH_2$—(C═O)—$CH_3$ is the residue of the second compound minus both the ene group and the diketone group. The product, which is an example primer compound (3) of formula HS-$Q^1$-S—$CH_2CH_2$-$Q^2$-(C═O)—$CH_2$—(C—O)—$CH_3$, has both a thiol group and a diketone group. As noted above, however, the primer compound can have more than one diketone group and more than one thiol group but is shown with only one thiol group and one diketone group in Reaction Scheme A for ease of explanation.

Reaction Scheme A

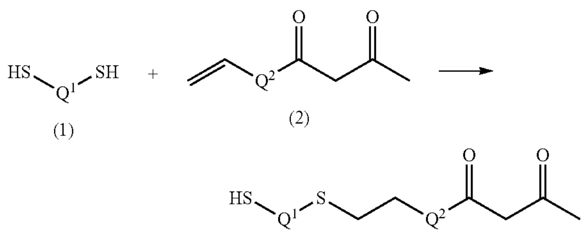

(1) (2)

(3)

Each of the first and second compounds are described more completely below.

First Compound Having a Plurality of Thiol Groups

The first compound included in the reaction mixture to form the primer compound contains at least two thiol groups. There are often two, three, or four thiol groups but more can be included, if desired. If the first compound has more than two thiol groups, there can be one, two, or three unreacted thiol groups in the primer compound. The first compound typically does not have any other group other than the thiol group that can react with the second compound. The thiol group is typically connected to a —$CH_2$— group or a —$CH(CH_3)$— group. In many embodiments, the thiol group is connected to a —$CH_2$— group.

The first compound is a heterohydrocarbon compound and usually contains other heteroatoms in addition to the at least two thiol groups. For example, the heterohydrocarbon compound often contains an oxy group (—O—), imino group (—NH—), carbonyl group (—(C═O)—), carbonyloxy group (—(C═O)—O—), carbonylimino group (—(C═O)—NH—), ether group (i.e., alkylene-oxy-alkylene group), oxy-alkylene group, oxy-alkylene-oxy group, heterocyclic ring, or the like, and combination thereof. The molecular weight (weight average molecular weight) of the first compound is often no greater than 1000 but higher molecular weight first compounds can be used, if desired. The molecular weight if often no greater than 900, no greater than 800, no greater than 600, no greater than 500, no greater than 400, or no greater than 300 grams/mole Some examples of the first compound are of Formula (I) and have more than two thiol groups.

(I)

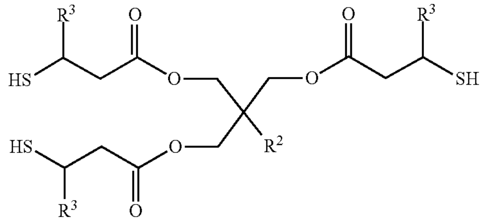

In Formula (I), group $R^2$ is methyl, ethyl, or —$CH_2$—O—(C═O)—$CH_2CHR^3$—SH and $R^3$ is hydrogen or methyl. Compounds of Formula (I) have three or four carbonyloxy groups. Example first compounds that are of Formula (I) include pentaerythritol tetrakis(3-mercaptopropionate), trimethylolpropane tris(3-mercaptopropionate), and 2-hydroxymethyl-2-methyl-1,3-propanediol tris-(3-mercaptopropionate). Some compounds of Formula (I) are available, for example, under the trade designation KARENZ MT (Tokyo, Japan) and Millipore Sigma (Saint Louis, MO, USA). After reaction with the second compound, there can be 1, 2, or 3 unreacted thiol groups in the resulting primer compound. It is noted that the product of the reaction may be a mixture of compounds.

Another first compound that has more than two thiol groups is of Formula (II).

(II)

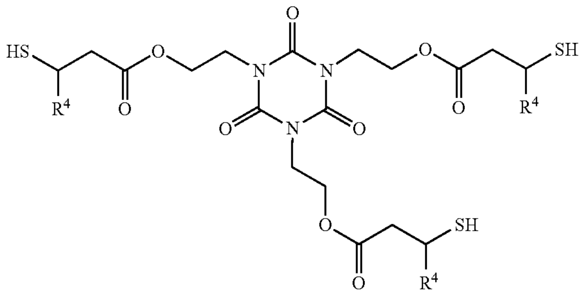

where each group $R^4$ is hydrogen or methyl. After rection with the second compound, there can be 1 or 2 unreacted thiol groups in the resulting primer compound. Compounds of Formula (II) include tris [2-(3-mercaptopropionyloxy) ethyl]isocyanurate and 1,3,5-tris(3-melcaptobutyloxethyl)-1,3,5-triazine-2,4,6 (1H,3H,5H)-trione. Some compounds of Formula (II) are available, for example, under the trade designation KARENZ MT (Tokyo, Japan) and Millipore Sigma (Saint Louis, MO, USA). After rection with the second compound, there can be 1 or 2 unreacted thiol groups in the resulting primer compound. It is noted that the product of the reaction may be a mixture of compounds.

Some first compounds have only two thiol groups such as those of Formula (III) that include an ether or polyether group.

(III)

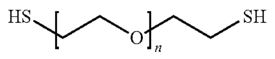

The variable n in Formula (III) is usually an integer in a range of 1 to 10 but can be larger, if desired. First compounds of Formula (II) include, for example, 2,2'-(ethylenedioxy) diethanethiol, tetra(ethylene glycol)dithiol, hexa (ethylene glycol)dithiol, and ethylene glycol bis-mercaptoacetate. After reaction with the second compound, there can be one unreacted thiol group in the resulting primer compound. Some compounds of Formula (III) are available from Millipore Sigma (Saint Louis, MO, USA). It is noted that the product of the reaction may be a mixture of compounds, but the main reaction product (i.e., the major component of the mixture) has one unreacted thiol group.

Other first compounds that have only two thiol groups are of Formula (IV).

(IV)

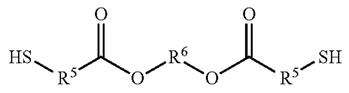

In Formula (IV), group $R^5$ is an alkylene having 1 to 4 carbon atoms where each $R^5$ group has a —$CH_2$— or —$CH(CH_3)$— group adjacent to the thiol group. Group $R^6$ is an alkylene having 1 to 6 carbon atoms. Each First compounds of Formula (III) include, for example, 1,4-butanediol bis(3-mercaptopropionate), 1,4-bis(3-mercaptobutyryloxy) butane, and ethylene glycol bis-mercaptoacetate. After rection with the second compound, there can be one unreacted thiol groups in the resulting primer compound. Some such compounds are available, for example, under the trade designation KARENZ MT (Tokyo, Japan) and Millipore Sigma (Saint Louis, MO, USA). It is noted that the product of the reaction may be a mixture of compounds, but the main reaction product (i.e., the major component of the mixture) has one unreacted thiol group.

Yet another first compound is of Formula (V)

$$C(CH_3)—[CH_2—(C_3H_6—O)_y—O—CH_2—CH(OH)—CH_2—SH]3 \quad (V)$$

where y is an integer equal to 1 or 2. Such compounds are commercially available from Huntsman (The Woodlands, Texas, USA) under the trade designation CAPCURE (e.g., CAPCURE 3-800). After rection with the second compound, there can be 1 or 2 unreacted thiol groups in the resulting primer compound. It is noted that the product of the reaction may be a mixture of compounds.

Second Compound Having an Ethylenically Unsaturated Group and a Diketone Group

The second compound included in the reaction mixture to form the primer compound contains an ethylenically unsaturated group plus a diketone group. Although the second compound can include more than one ethylenically unsaturated group and/or more than one diketone group, most second compounds contain only one of each type of group. The ethylenically unsaturated group, which has an ene group, can react with a thiol group in the first compound. The second compound typically does not have any other group other than the ene group that can react with the first compound.

The second compound is a heterohydrocarbon compound and optionally contains heteroatoms in addition to those included in the diketone group. These other groups can be an oxy group, imino group, carbonyloxy group, carbonylimino group, oxy-alkylene group, oxy-alkylene-oxy group, alkylene-oxy-alkylene group, heterocyclic ring, or the like and combinations thereof. The molecular weight (weight average molecular weight) of the second compound is often no greater than 1000, no greater than 900, no greater than 800, no greater than 600, no greater than 500, no greater than 400, or no greater than 300 grams/mole but higher molecular weight second compound can be used, if desired.

Some examples of the second compound contain an allyl group such as in compounds of Formula (VI).

$$H_3C—(C{=}O)—CH_2—(C—O)—O[—CH_2CH_2—O]_x—CH_2CH{=}CH_2 \quad (VI)$$

wherein the variable x is usually 0 or 1 but can be a larger number such as up to 5, up to 4, up to 3, or up to 2. These examples contain an oxy or at least one oxy-alkylene-oxy group between the allyl and diketone groups. Examples of second compounds of Formula (VI) are 4-allylacetoacetate and 2-(allyloxy)ethyl acetoacetate.

Other example second compounds contain an ene group separated from the diketone group by an alkylene group. Such compounds are of Formula (VII)

$$H_3C—(C{=}O)—CH_2—(C—O)—R^7—CH{=}CH_2 \quad (VII)$$

where $R^7$ is an alkylene having 2 to 6 carbon atoms. Examples of second compounds of Formula (VII) are non-8-ene-2,4-dione and dec-9-ene-2,4-dione.

Still other example second compounds contain a (meth)acryloyloxy group. Such second compounds are often of Formula (VIII)

$$H_3C—(C—O)—CH_2—(C{=}O)—O—R^8—O—(C{=}O)—CR^1—CH_2 \quad (VIII)$$

wherein $R^8$ is an alkylene having 2 to 6 carbon atoms and $R^1$ is hydrogen or methyl. Examples of second compounds of Formula (VI) are 2-(methacryloyloxy)ethyl acetoacetate and 2-(acryloyloxy)ethyl acetoacetate, and 1-(prop-2-enoyloxy)propan-2-yl 3-oxabutaneoate.

Preparation of Primer Compound

Any suitable method can be used to form the primer compound. In some embodiments, the first and second compounds are combined in amounts sufficient to react at least one mole of the second compound with every mole of the first compound. An optional organic solvent that is miscible with both compounds plus the primer compound can be present. The organic solvent is typically selected so that it does not react with the first and second compounds used to form the primer compound. Further, the organic solvent is usually selected to have a boiling point that is no greater than 120 degrees Celsius such as no greater than 110 degrees Celsius or no greater than 100 degrees Celsius. Suitable solvents include, but are not limited to, ethyl acetate, acetone, tetrahydrofuran, methyl ethyl ketone, methyl isobutyl ketone, acetonitrile, butanol, isopropanol, benzene, toluene, or a combination thereof. In some embodiments, the reaction mixture contains 0 to 60 weight percent of the optional organic solvent.

In addition to the first compound and the second compound, the reaction mixture often contains an initiator that is a photoinitiator active in the UV-visible region of the electromagnetic spectrum or a thermal initiator. The initiator is often added in an amount in a range of 0 to 5 weight percent based on the total weight of the reactants (i.e., the first and second compounds). The amount is often at least 0.1, at least 0.5, at least 1, at least 1.5, at least 2, at least 2.5 and up to 5, up to 4.5, up to 4, up to 3.5, up to 3, up to 2.5, or up to 2 weight percent based on the total weight of the reactants in the reaction mixture.

Exemplary thermal initiators include various azo compound such as those commercially available under the trade designation VAZO from Chemours Co. (Wilmington, DE, USA) including VAZO 67, which is 2,2'-azobis(2-methylbutane nitrile), VAZO 64, which is 2,2'-azobis(isobutyronitrile), VAZO 52, which is (2,2'-azobis(2,4-dimethylpentanenitrile), and VAZO 88, which is 1,1'-azobis(cyclohexanecarbonitrile); various peroxides such as benzoyl peroxide, cyclohexane peroxide, lauroyl peroxide, di-tert-amyl peroxide, tert-butyl peroxy benzoate, di-cumyl peroxide, and peroxides commercially available from Atofina Chemical, Inc. (Philadelphia, PA, USA) under the trade designation LUPERSOL (e.g., LUPERSOL 101, which is 2,5-bis(tert-butylperoxy)-2,5-dimethylhexane, and LUPERSOL 130, which is 2,5-dimethyl-2,5-di-(tert-butylperoxy)-3-hexyne); various hydroperoxides such as tert-amyl hydroperoxide and tert-butyl hydroperoxide; and mixtures thereof.

In many embodiments, a photoinitiator is used to form the primer compound. Some exemplary photoinitiators are benzoin ethers (e.g., benzoin methyl ether or benzoin isopropyl ether) or substituted benzoin ethers (e.g., anisoin methyl ether). Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, NJ, USA) or under the trade designation ESACURE KB-1 from Sartomer (Exton, PA, USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione- 2-(0-ethoxycarbonyl) oxime. Other suitable photoinitiators include, for example, 1-hydroxycyclohexyl phenyl ketone (commercially available under the trade designation IRGACURE 184), bis(2,4,6-trimethylbenzoyl)phenyl phosphine oxide (commercially available under the trade designation IRGACURE 819), 1-[4-(2-hydroxyethoxy)phenyl]-2-hydroxy-2-methyl-1-propane-1-one (commercially available under the trade designation IRGACURE 2959), 2-benzyl-2-dimethylamino-1-(4-morpholinophenyl) butanone (commercially available under the trade designation IRGACURE 369), 2-methyl-1-[4-(methylthio)phenyl]-2-morpholinopropan-1-one (commercially available under the trade designation IRGACURE 907), and 2-hydroxy-2-methyl-1-phenyl propan-1-one (commercially available under the trade designation DAROCUR 1173 from Ciba Specialty Chemicals Corp. (Tarrytown, NY, USA)).

The thiol-ene reaction of the first compound with the second can occur under any known reaction conditions. In some embodiments, the reaction occurs at or near room temperature (e.g., in a range of 20 to 30 degree Celsius) in the presence of ultraviolet radiation. Black ultraviolet light sources that emit long wavelength (UV-A) ultraviolet light and very little visible light are often preferred. In other embodiments, the reaction occurs at elevated temperatures (e.g., up to 60 degrees Celsius, up to 50 degrees Celsius, or up to 40 degrees Celsius). The reaction time is typically less than 10 hours, less than 8 hours, less than 5 hours, or less than 2 hours.

Articles

Various types of articles of increasing complexity are provided. The most basic article, which can be referred to as a “first article”, contains a first metal-containing substrate and a first surface of a first primer layer positioned adjacent to the first metal-containing substrate. That is, the first article is arranged in the following order: (1) first metal-containing substrate and (2) first primer layer. The first primer layer comprises a first primer compound as described above. The first primer compound is chelated to the first metal-containing substrate.

Other articles further contain at least one adhesive composition layer, which can be referred to as adhesive layer(s) indicating that there can be one or more layers. These articles can be referred to as a “second article”. The at least one adhesive layer is positioned adjacent to a second surface of the first primer layer opposite the first surface of the first primer layer. That is, the second article is arranged in the following order: (1) first metal-containing substrate, (2) first primer layer, and (3) adhesive layer(s).

Still other articles further contain an additional substrate and optionally an additional primer layer. These articles can be referred to as “third articles” and can be of two different constructions.

In a first embodiment, the third article includes the second article plus a second primer layer and a second metal-containing substrate. This first construction of the third article includes multiple layers arranged in the following order: first metal-containing substrate, first primer layer, at least one adhesive layer, second primer layer, and second metal-containing substrate. Both the first primer layer and the second primer layer include the primer compound described herein. The second primer compound in the second primer layer is chelated to the second metal-containing substrate.

In a second embodiment, the third article includes the second article plus a second substrate and an optional second primer layer. This second construction of the third article includes multiple layers arranged in the following order: first metal-containing substrate, first primer layer, at least one adhesive layer, an optional second primer layer, and a second substrate. The second substrate may be a metal-containing substrate or a non-metal containing substrate. The optional second primer layer can contain a primer compound as described herein, a different type of primer compound, or no primer compound.

The adhesive layer(s) in either the second article or the third article can be pressure-sensitive adhesives. The adhesive layer(s) can be bonded to the first primer layer in the second article or to both the first primer layer and to the second primer layer in the third article.

Starting with the first articles, a primer layer is positioned adjacent to a metal-containing substrate. The primer layer is formed on the metal-containing substrate using a primer composition that includes both the primer compound as described herein and an organic solvent. The organic solvent is typically selected to be easily removed after deposition of the primer composition on the metal-containing substrate. Most of the organic solvent is removed by drying (e.g., evaporation or heating) to form the primer layer.

Any suitable metal-containing substrate can be used. For example, the substrate can contain metals, metal oxides, metal alloys, metal-containing ceramic materials, or mixture thereof. In some embodiments, the first article contains a steel-containing substrate, a copper-containing substrate, an iron-containing substrate, a zinc-containing substrate, a chromium-containing substrate, a nickel-containing substrate, a zirconium-containing substrate, or a combination thereof. For example, the steel-containing substrate can be stainless steel or galvanized steel and the copper-containing substrate can be copper, bronze, or brass. In some embodiments, the substrate contains a copper-containing substrate.

The primer layer is typically formed on the metal-containing substrate with a primer composition. The primer composition contains various materials dissolved in an organic solvent such that the solid content is in a range of about 1 to about 20 weight percent based on a total weight of the primer composition. The solids typically include the primer compound and other optional compounds such as, for example, a fluorescent compound or dye (e.g., an ultraviolet or visible dye). The fluorescent compound or dye can provide a means of verifying that the primer layer has been applied to the metal-containing substrate. The percent solids can be at least 1, at least 2, at least 3, or at least 5 weight percent and up to 20, up to 18, up to 15, up to 12, up to 10, up to 8, up to 7, or up to 5 weight percent based on a total weight of the primer composition.

Typically, at least 80 weight percent of the solid content is the primer compound as described herein. For example, at least 85, at least 90, at least 95, at least 98, or at least 99, at least 99.5, or 100 weight percent of the solid content of the primer composition is the primer compound. The remainder of the primer composition (i.e., the portion of the primer composition that is not a solid) is typically an organic solvent selected, for example, from those organic solvents described above for use in preparation of the primer compound.

Any suitable method can be used to position the first primer composition adjacent to a first surface of a metal-containing substrate. For example, the primer composition can be applied using a sponge, roller, swab, or the like. Alternatively, the primer composition can be applied to the substrate by dip coating or by spraying. In most embodiments, the primer composition is applied to completely cover the first surface of the metal-containing substrate. The second primer composition in the third article can be positioned adjacent to the second metal-containing substrate in the same manner.

After application, the first primer composition is dried to form the first primer layer. Any suitable drying method can be used such as evaporation at room temperature or heating at a temperature above room temperature that is sufficient to volatilize the organic solvent within a desired amount of time. The temperature is often no greater than about 100, no greater than 80, no greater than 60, no greater than 50, or no greater than 40 degrees Celsius. No special atmosphere is needed. The second primer layer in the third article can be formed adjacent to the second substrate in the same manner.

Although any suitable thickness can be used, the thickness of the first primer layer on the first metal-containing substate is often no greater than 100, no greater than 90, no greater than 80, no greater than 70, no greater than 60, or no greater than 50 micrometers. The thickness is sufficient to completely cover at least one surface of the metal-containing substrate. The thickness of the second primer layer on the second metal-containing substrate in the third article is like that of the first primer layer in the first article.

Second articles can be prepared from the first articles. More specifically, second articles are provided that contain (1) a first metal-containing substrate, (2) a first primer layer comprising a first primer compound as described herein, and (3) at least one adhesive layer. To form the second article, a first surface of the first primer layer is positioned adjacent the first metal-containing substrate. At least one adhesive layer is positioned adjacent to a second surface of the first primer layer opposite the first surface of the first primer layer. If there is a single adhesive layer, it is typically a pressure-sensitive adhesive layer. If there are multiple adhesive layers, which can be referred to as a multilayer adhesive, two adhesive layers are usually arranged on either side of a core that may optionally be foamed and that may optionally be an adhesive composition. That is, the multilayer adhesive contains a first outer adhesive layer that is often referred to as a first skin layer, a core layer, and a second outer adhesive layer that is often referred to as a second skin layer. Typically, the two skin layers each contain a pressure-sensitive adhesive.

In the second article, the first primer compound within the first primer layer can chelate with the first metal-containing substrate through the acetoacetate group. Additionally, the thiol group of the first primer compound can interact with components in the adhesive layer(s) positioned adjacent to the first primer layer. This interaction may be, for example, the formation of a thioester linkage (—(C—O)—S—) by reacting thiol groups on the primer compound with various monomeric units having a carbonyloxy linkage (—(C=O)—O—) within the adhesive layer(s). The formation of this linkage group can result in the incorporation of the primer compound into the polymeric matrix of the adhesive layer(s).

A third article is provided that includes the second article plus a second substrate and an optional primer layer. The second substrate can be a metal-containing substrate or a non-metal-containing substrate and can be prepared from any desired material such as a polymer, glass, ceramic, metal, or combinations thereof. The optional primer layer, if present, can contain a primer compound as described herein or a different type of primer compound.

Some third article include the second article plus an additional primer layer and an additional metal-containing substrate (e.g., second metal-containing substrate). More specifically, these third articles contain (1) a first metal-containing substrate, (2) a first primer layer comprising a first primer compound as described herein, (3) at least one adhesive composition layer, (4) a second primer layer comprising a second primer compound as described herein, and (5) a second metal-containing substrate. To form this third article, a first surface of the first primer layer is positioned adjacent the first metal-containing substrate. A first surface of the adhesive layer(s) is positioned adjacent to a second surface of the first primer layer opposite the first surface of the first primer layer and the first metal-containing substrate. A first surface of a second primer composition is positioned adjacent to a second surface of the adhesive layer(s) opposite the first surface of the at adhesive layer(s). The second primer composition contains a second primer compound that can be the same or different than the first primer compound but both primer compounds are those described above. A second metal-containing substrate is positioned adjacent to a second surface of the second primer layer opposite the first surface of the second primer layer.

In these third article with two primer layers containing primer compounds as described above, the first primer compound in the first primer layer can chelate with the first metal-containing substrate and the second primer compound in the second primer layer can chelate with the second metal-containing substrate in the second primer layer. The thiol groups in both the first primer compound and the second primer compound can interact with components in the adhesive layer positioned adjacent to each primer layer. This can be a single adhesive layer or multilayer adhesive such as one having a shell-core-shell configuration where the shell layers are pressure-sensitive adhesive layers. This interaction with the adhesive layer(s) may be, for example, the reaction of a thiol group of the primer with various monomeric units having carbonyloxy linkages (—(C=O)—O—) in the adhesive layer(s) forming a thioester linkage (—(C=O)—S—). The formation of this linkage group can result in the incorporation of the primer compound into the polymeric matrix of the adhesive layer. Thus, the first primer layer is attached to the first metal-containing substrate through chelation and to the adhesive layer(s) through a covalent bond. Further, the second primer layer is attached to the second metal-containing substrate through chelation and to the adhesive layer(s) through a covalent bond. The formation of the covalent bonds result in the incorporation of a first reacted primer compound and the second reacted primer compound into the polymeric matrix of the adhesive composition.

Other third articles include the second article plus a second substrate and an optional second primer layer. This second construction of the third article includes multiple layers arranged in the following order: first metal-containing substrate, first primer layer, at least one adhesive layer, an optional second primer layer, and a second substrate. The second substrate may be a metal-containing substrate or a non-metal containing substrate. The optional second primer layer can contain a primer compound as described herein, a different type of primer compound, or no primer compound. If the second substrate is a non-metal containing substrate, there is often no second primer layer or a different type of primer layer other than those described herein is used.

Adhesive Layer(s)

In most embodiments, the at least one adhesive layer contains a (meth)acrylate copolymer and functions as a pressure-sensitive adhesive. For use as a pressure-sensitive adhesive, the monomers selected to form the (meth)acrylate copolymer are typically those that will result in an elastomeric material. The elastomeric material typically has a glass transition temperature (Tg) that is no greater than 20° C., no greater than 10° C., no greater than 0° C., no greater than −10° C., no greater than −20° C., no greater than −30° C., no greater than −40° C., or no greater than −50° C. The glass transition temperature can be measured using techniques such as Differential Scanning calorimetry and Dynamic Mechanical Analysis. Alternatively, the glass transition temperature can be estimated using the Fox equation. Lists of glass transition temperatures for homopolymers are available from multiple monomer suppliers such as from BASF Corporation (Houston, TX, USA), Polyscience, Inc. (Warrington, PA, USA), and Aldrich (Saint Louis, Missouri, USA) as well as in various publications such as, for example, Mattioni et al., *J. Chem. Inf. Comput. Sci.,* 2002, 42, 232-240.

To form an elastomeric (meth)acrylate copolymer, the monomeric composition often contains at least one low Tg monomer. As used herein, the term "low Tg monomer" refers to a monomer having a Tg no greater than 20° C. when homopolymerized (i.e., a homopolymer formed from the low Tg monomer has a Tg no greater than 20° C.). Suitable low Tg monomers are often selected from alkyl (meth) acrylates, heteroalkyl (meth)acrylates, aryl substituted alkyl acrylates, and aryloxy substituted alkyl acrylates.

Example low Tg alkyl (meth)acrylate monomers often are non-tertiary alkyl acrylates but can be an alkyl methacrylate having a linear alkyl group with at least 4 carbon atoms. Specific examples of alkyl (meth)acrylates include, but are not limited to, methyl acrylate, ethyl acrylate, n-propyl acrylate, n-butyl acrylate, n-butyl methacrylate, isobutyl acrylate, sec-butyl acrylate, n-pentyl acrylate, 2-methylbutyl acrylate, n-hexyl acrylate, cyclohexyl acrylate, 4-methyl-2-pentyl acrylate, 2-methylhexyl acrylate, 2-ethylhexyl acrylate, n-octyl acrylate, 2-octyl acrylate, isooctyl acrylate, isononyl acrylate, isoamyl acrylate, n-decyl acrylate, isodecyl acrylate, n-decyl methacrylate, lauryl acrylate, isotridecyl acrylate, n-octadecyl acrylate, isostearyl acrylate, and n-dodecyl methacrylate.

Example low Tg heteroalkyl (meth)acrylate monomers often have at least 3, at least 4, or at least 6 carbon atoms and can have up to 30 or more, up to 20, up to 18, up to 16, up to 12, or up to 10 carbon atoms. Specific examples of heteroalkyl (meth)acrylates include, but are not limited to, 2-ethoxyethyl acrylate, 2-(2-ethoxyethoxy)ethyl acrylate, 2-methoxyethyl (meth)acrylate, and tetrahydrofurfuryl (meth)acrylate.

Exemplary aryl substituted alkyl acrylates or aryloxy substituted alkyl acrylates include, but are not limited to, 2-biphenylhexyl acrylate, benzyl acrylate, 2-phenoxyethyl acrylate, and 2-phenylethyl acrylate.

The monomer composition used to form the (meth)acrylate copolymer often contains at least 40 weight percent of a low Tg monomer based on a total weight of monomers in monomer composition 1A. In some embodiment, the monomer composition contains at least 45, at least 50, at least 60, at least 65, at least 70, at least 75, or at least 80 weight percent and up to 100, up to 99, up to 98, up to 95, up to 90, or up to 85 weight percent of the low Tg monomer.

The monomer compositions usually include a polar monomer. The polar monomer has an ethylenically unsaturated group plus a polar group such as an acidic group or a salt thereof, a hydroxyl group, a primary amido group, a secondary amido group, a tertiary amido group, an amino group, an ether group, or an epoxy group. Having a polar monomer often facilitates adherence of the pressure-sensitive adhesive to a variety of substrates. It is often this group that can react with an epoxy group on the primer compound.

Exemplary polar monomers with an acidic group include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinyl phosphonic acid, and mixtures thereof. Due to their availability, the acid monomers are often (meth)acrylic acids.

Exemplary polar monomers with a hydroxyl group include, but are not limited to, hydroxyalkyl (meth)acrylates (e.g., 2-hydroxyethyl (meth)acrylate, 2-hydroxypropyl (meth)acrylate, 3-hydroxypropyl (meth)acrylate, and 4-hydroxybutyl (meth)acrylate), hydroxyalkyl (meth)acrylamides (e.g., 2-hydroxyethyl (meth)acrylamide or 3-hydroxypropyl (meth)acrylamide), ethoxylated hydroxyethyl (meth) acrylate (e.g., monomers commercially available from Sartomer (Exton, PA, USA) under the trade designation CD570, CD571, and CD572), and aryloxy substituted hydroxyalkyl (meth)acrylates (e.g., 2-hydroxy-2-phenoxypropyl (meth)acrylate).

Exemplary polar monomers with a primary amido group include (meth)acrylamide. Exemplary polar monomers with secondary amido groups include, but are not limited to, N-alkyl (meth)acrylamides such as N-methyl(meth)acrylamide, N-ethyl(meth)acrylamide, N-isopropyl(meth)acrylamide, N-tert-octyl(meth)acrylamide, or N-octyl(meth)acrylamide. Exemplary polar monomers with a tertiary amido group include, but are not limited to, N-vinyl caprolactam, N-vinyl-2-pyrrolidone, (meth)acryloyl morpholine, and N,N-dialkyl (meth)acrylamides such as N,N-dimethyl (meth)acrylamide, N,N-diethyl(meth)acrylamide, N,N-dipropyl(meth)acrylamide, and N,N-dibutyl(meth)acrylamide.

Polar monomers with an amino group include various N,N-dialkylaminoalkyl (meth)acrylates and N,N-dialkylaminoalkyl (meth)acrylamides. Examples include, but are not limited to, N,N-dimethyl aminoethyl (meth)acrylate, N,N-dimethylaminoethyl(meth)acrylamide, N,N-dimethylaminopropyl (meth)acrylate, N,N-dimethylaminopropyl (meth)acrylamide, N,N-diethylaminoethyl (meth)acrylate, N,N-diethylaminoethyl(meth)acrylamide, N,N-diethylaminopropyl (meth)acrylate, and N,N-diethylaminopropyl (meth)acrylamide.

Polar monomers with an epoxy group include, for example, glycidyl (meth)acrylate.

Polar monomers with ether linkages include those that contain poly(alkylene oxide) segments such as poly(ethylene oxide) (meth)acylate, poly(propylene oxide) (meth) acylate, poly(tetramethylene oxide) (meth)acrylate, di(ethylene glycol)ethyl ether (meth)acrylate, and the like. Any suitable molecular weight monomer can be used.

The amount of the polar monomer is often in a range of 0.5 to 30 weight percent based on the weight of monomers in monomer composition. The amount of polar monomer is often at least 1, at least 2, at least 3, or at least 5 weight percent based on the total weight of monomers in monomer composition. The amount can be up to 30, up to 25, up to 20, up to 15, up to 10, or up to 5 weight percent. For example, the amount is often in a range of 0.5 to 30, 0.5 to 20, 1 to 20, 1 to 10, 1 to 5, 0.5 to 15, 1 to 15, or 1 to 10 weight percent based on a total weight of monomers in monomer composition.

The monomer composition can optionally include a high Tg monomer. As used herein, the term "high Tg monomer" refers to a monomer that has a Tg greater than 30° C., greater than 40° C., or greater than 50° C. when homopolymerized (i.e., a homopolymer formed from the monomer has a Tg greater than 30° C., greater than 40° C., or greater than 50° C. Some suitable high Tg monomers have a single (meth) acryloyl group such as, for example, methyl methacrylate, ethyl methacrylate, n-propyl methacrylate, isopropyl methacrylate, n-butyl methacrylate, isobutyl methacrylate, sec-butyl methacrylate, tert-butyl (meth)acrylate, cyclohexyl methacrylate, isobornyl (meth)acrylate, stearyl (meth)acrylate, phenyl acrylate, benzyl methacrylate, 3,3,5 trimethylcyclohexyl (meth)acrylate, 2-phenoxyethyl methacrylate, N-octyl(meth)acrylamide, and mixtures thereof. Other suitable high Tg monomers have a single vinyl group that is not a (meth)acryloyl group such as, for example, various vinyl ethers (e.g., vinyl methyl ether), vinyl esters (e.g., vinyl acetate and vinyl propionate), styrene, substituted styrene (e.g., α-methyl styrene), vinyl halide, and mixtures thereof. Vinyl monomers having a group characteristic of polar monomers are considered herein to be polar monomers.

The amount of high Tg monomer can be up to 50 weight percent or even higher provided that the Tg of the (meth) acrylate copolymer is no greater than 20° C. In some embodiments, the amount can be up to 40, up to 30, up to 20, up to 15, or up to 10 weight percent. The amount can be at least 1, at least 2, or at least 5 weight percent. For example, the amount can be in a range of 0 to 50, 0 to 40, 0 to 30, 0 to 20, 0 to 10, 1 to 30, 1 to 20, or 1 to 10 weight percent. The amount values are based on a total weight of monomers in monomer composition.

Still further, the monomer composition can optionally include a vinyl monomer (i.e., a monomer with an ethylenically unsaturated group that is not a (meth)acryloyl group). Examples of optional vinyl monomers include, but are not limited to, various vinyl ethers (e.g., vinyl methyl ether), vinyl esters (e.g., vinyl acetate and vinyl propionate), styrene, substituted styrene (e.g., α-methyl styrene), vinyl halide, and mixtures thereof. The vinyl monomers having a group characteristic of polar monomers are considered herein to be polar monomers.

The amount of the optional vinyl monomer lacking a (meth)acryloyl group is often in a range of 0 to 15 weight percent based on the weight of monomers in monomer composition. If present, the amount of vinyl monomers in the monomer composition is often at least 0.1, 0.2, 0.5, or 1 weight percent based on the total weight of monomers in the monomer composition. The amount can be up to 15, up to 10, or up to 5 weight percent. For example, the amount is often in a range of 0 to 15, 0.1 to 10, 0.5 to 5, or 1 to 5 weight percent based on a total weight of monomers in the monomer composition.

Further, various crosslinking monomers having multiple (meth)acryloyl groups can be included in the monomer composition. Suitable crosslinking monomers often contain at least two acryloyl groups. Exemplary crosslinking monomers with two acryloyl groups include 1,2-ethanediol diacrylate, 1,3-propanediol diacrylate, 1,4-butanediol diacrylate, 1,4-butanediol diacrylate, 1,6-hexanediol diacrylate (HDDA), 1,9-nonanediol diacrylate, 1,12-dodecanediol diacrylate, butylene glycol diacrylate, bisphenol A diacrylate, diethylene glycol diacrylate, triethylene glycol diacrylate, tetraethylene glycol diacrylate, tripropylene glycol diacrylate, polyethylene glycol diacrylate, polypropylene glycol diacrylate, polyethylene/polypropylene copolymer diacrylate, and neopentylglycol hydroxypivalate diacrylate modified caprolactone. Exemplary crosslinking monomers with three or four (meth)acryloyl groups include, but are not limited to, trimethylolpropane triacrylate (e.g., commercially available under the trade designation TMPTA-N from Surface Specialties, Smyrna, GA and under the trade designation SR-351 from Sartomer, Exton, PA), pentaerythritol triacrylate (e.g., commercially available under the trade designation SR-444 from Sartomer), tris(2-hydroxyethylisocyanurate)triacrylate (commercially available under the trade designation SR-368 from Sartomer), a mixture of pentaerythritol triacrylate and pentaerythritol tetraacrylate (e.g., commercially available from Surface Specialties under the trade designation PETIA with an approximately 1:1 ratio of tetraacrylate to triacrylate and under the trade designation PETA-K with an approximately 3:1 ratio of tetraacrylate to triacrylate), pentaerythritol tetraacrylate (e.g., commercially available under the trade designation SR-295 from Sartomer), di-trimethylolpropane tetraacrylate (e.g., commercially available under the trade designation SR-355 from Sartomer), and ethoxylated pentaerythritol tetraacrylate (e.g., commercially available under the trade designation SR-494 from Sartomer). An exemplary crosslinking monomer with five (meth)acryloyl groups includes, but is not limited to, dipentaerythritol pentaacrylate (e.g., commercially available under the trade designation SR-399 from Sartomer).

The monomer composition often includes 0 to 20 weight percent crosslinking monomer based on a total weight of polymerized and polymerizable material. In many embodiments, the crosslinkable composition contains at least 0.01, at least 0.05, at least 0.1, at least 0.5, or at least 1 weight percent and up to 15, up to 10, up to 5, or up to 1 weight percent crosslinking monomer based on the total weight of the monomer composition.

Overall, the (meth)acrylate copolymer can be formed from a monomer composition that contains 40 to 99.5 weight percent of the low Tg monomer, 0.5 to 30 weight percent polar monomer, 0 to 50 weight percent high Tg monomer, 0 to 15 weight percent vinyl monomers not having a (meth)acryloyl group, and 0 to 20 weight percent crosslinking monomer. In other embodiments, the monomer composition contains 40 to 99 weight percent of the low Tg monomer, 1 to 30 weight percent polar monomer, 0 to 50 weight percent high Tg monomer, 0 to 15 weight percent vinyl monomers not having a (meth)acryloyl group, and 0 to 10 weight percent crosslinking monomer. In still other embodiments, the monomer composition contains 60 to 99 weight percent of the low Tg monomer, 1 to 20 weight percent polar monomer, 0 to 40 weight percent high Tg monomer, 0 to 10 weight percent vinyl monomers not having a (meth)acryloyl group, and 0 to 10 weight percent crosslinking monomer. In yet other embodiments, the monomer composition contains 75 to 99 weight percent of the low Tg monomer, 1 to 10 weight percent polar monomer, 0 to 25 weight percent high Tg monomer, 0 to 5 weight percent vinyl monomers not having a (meth)acryloyl group, and 0 to 10 weight percent crosslinking monomer.

The weight average molecular weight of the (meth) acrylate copolymer is often in a range of 10,000 Da to 1,000,000 Da or even higher when the (meth)acrylate copolymer is crosslinked. For example, the weight average molecular weight can be at least 20,000 Da, at least 30,000 Da, at least 40,000 Da, or at least 50,000 and can be up to 1,000,000 Da, up to 900,000 Da, up to 800,000 Da, up to 700,000 Da, or up to 600,000 Da.

An initiator is typically added to the monomer composition to prepare the (meth)acrylate copolymer. Any photoinitiator or thermal initiator listed above for preparation of the primer compound can be used as the initiator for the polymerization reaction. The amount of the initiator is often in a range of 0.01 to 1 weight percent based on a total weight of monomers in the monomer composition.

As a further option, the adhesive composition can optionally include one or more additives such as, for example, fillers, plasticizers, tackifiers, chain transfer agents, fibrous reinforcing agents, woven and non-woven fabrics, foaming agents, antioxidants, stabilizers, fire retardants, viscosity enhancing agents, coloring agents, and mixtures thereof.

If the adhesive layer is a single layer, any desired thickness can be used. In some embodiments, the thickness of the single adhesive layer is in a range of 25 to 100 micrometers. The thickness can be at least 25, at least 30, at least 35, at least 40, at least 45, at least 50, at least 55, or at least 60 micrometers and up to 100 or greater, up to 95, up to 90, up to 85, up to 80, up to 75, up to 70, up to 65, up to 60, up to 55, or up to 50 micrometers.

In some embodiments, the at least one adhesive composition layer is in the form of a three-layered adhesive composition. The three-layer adhesive composition has a first adhesive skin layer, a core layer, and a second adhesive skin layer. Each of the first and second skin layers often contain an adhesive composition containing a (meth)acrylate copolymer as described above. The skin layers are typically pressure-sensitive adhesives.

The core typically contains polymeric foam. The composition of the foam core is often a (meth)acrylic-based copolymer or a silicone polymer. Further preferred foam compositions include foams that are essentially free of any polyurethanes, which tend to degrade when exposed to ultraviolet light. For example, the foam composition could have less than 5 percent, less than 3 percent, less than 1 percent, less than 0.5 percent or less than 0.1 percent polyurethanes.

(Meth)acrylic-based copolymer foams and silicone foams are useful due to their ultraviolet light stability, conformability, and ability to distribute stress. The (meth)acrylic-based foams can be formed from the same types of monomers described above for preparation of the (meth)acrylate copolymers.

For example, any of the alkyl (meth)acrylates described above can be used. In some embodiments, the alkyl (meth) acrylates is selected to include, but is not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate.

To enhance the strength of the foam, the alkyl (meth) acrylate may be copolymerized with one or more polar monomers such as any of those described above. In some embodiments, the polar monomer is selected to include, but is not limited to, (meth)acrylic acid, itaconic acid, (meth) acrylamide, N-substituted acrylamides (for example, N,N-dimethyl acrylamide), (meth)acrylonitrile, hydroxyalkyl acrylates, cyanoethyl acrylate, N-vinylpyrrolidone, N-vinylcaprolactam, and maleic anhydride. In some embodiments, these polar monomers are used in amounts of less than 20 weight percent based on a total weight of polymerizable components in the reaction mixture used to form the foam. Is such, the resulting foam tends to be tacky at ordinary room temperatures. In some cases, however, the tackiness can be preserved at up to 50 percent by weight of N-vinylpyrrolidone.

Enhancement of the cohesive strength of the foam may also be achieved through the use of a crosslinking agent such as 1,6-hexanediol diacrylate, with a photoactive triazine crosslinking agent such as taught in U.S. Pat. No. 4,330,590 (Vesley) and U.S. Pat. No. 4,329,384 (Vesley et al.), or with a heat-activatable crosslinking agent such as a lower-alkoxylated amino formaldehyde condensate having $C_{1-4}$ alkyl groups such as, for example, hexamethoxymethyl melamine, tetramethoxymethyl urea, or tetrabutoxymethyl urea. Crosslinking may be achieved by irradiating the composition with electron beam (or "e-beam") radiation, gamma radiation, or x-ray radiation. Bisamide crosslinkers may be used with (meth)acrylic adhesives that are prepared in solution.

The (meth)acrylic-based polymer used in the foam can be prepared by any suitable polymerization method. Suitable polymerization methods include, but are not limited to, photopolymerization, thermal polymerization, or ionizing radiation polymerization. These methods can be carried out in solution, emulsion, or bulk without solvent. Bulk polymerization methods are described in U.S. Pat. No. 5,804,610 (Hamer et al.). Optionally, photopolymerizable monomers may be partially polymerized to a viscosity of from 1000 to 40,000 cps to facilitate coating. Alternatively, partial polymerization can be affected by heat. If desired, viscosity can also be adjusted by mixing monomers with a thixotropic agent such as fumed silica.

The weight average molecular weight of the polymer in the foam before crosslinking can be at least 600,000 g/mol, at least 800,000 g/mol, or at least 1,000,000 g/mol.

Polymerization can take place by exposure to ultraviolet radiation in an inert atmosphere such as under a blanket of nitrogen or argon gas. Alternatively, an inert environment can be achieved by forming a polymerizable composition layer and temporarily covering a polymerizable composition layer with a plastic film transparent to ultraviolet radiation and irradiating the composition through the film. If the polymerizable composition is not covered during polymerization, the permissible oxygen content of the inert atmosphere can be increased by mixing into the polymerizable composition an oxidizable tin compound such as disclosed in U.S. Pat. No. 4,303,485 (Levens), which can enable relatively thicker coatings to be polymerized in air.

Optionally, the foam contains one or more additives. Such additives can include, for example, fillers, antioxidants, viscosity modifiers, pigments, tackifying resins, fibers, flame retardants, antistatic and slip agents, thermally conductive particles, electrically conductive particles, continuous microfibers, filaments, and mixtures thereof.

The polymer used to make the foam may be initially coated onto and polymerized against a flexible backing sheet (for example, a release liner) that has a low-adhesion surface from which the polymerized layer is readily removable and almost always is self-sustaining. If the opposite face of the backing sheet also has a low-adhesion surface, the backing sheet with its polymerized layer may be wound up in roll form for storage prior to assembly of the finished adhesive article.

In some embodiments, the foam is made from a silicone polymer. Suitable silicone polymers can include, for example, an MQ resin containing a resinous core and non-resinous polyorganosiloxane group terminated with a silicon-bonded hydroxyl group; a treated MQ resin, and a polydiorganosiloxane terminated with a condensation reactive group. Such compositions may be used for structural glazing applications, as described in U.S. Pat. No. 8,298,367 (Beger et al.).

Generally, the foam may be an open cell foam, a closed cell foam, or combination thereof. In some embodiments, the foam is a syntactic foam containing hollow microspheres, for example, hollow glass microspheres. Useful hollow glass microspheres include those having a density of less than 0.4 g/cm and having a diameter of from 5 to 200 micrometers. The microspheres may be clear, coated, stained, or a combination thereof. The microspheres typically comprise from 5 to 65 volume percent of the foam composition. Examples of useful (meth)acrylic foams thus made are disclosed in U.S. Pat. No. 4,415,615 (Esmay et al.) and U.S. Pat. No. 6,103,152 (Gehlsen et al.).

In some embodiments, foams may be formed by blending expanded polymeric microspheres into a polymerizable composition. In some embodiments, foams may be formed by blending expandable polymeric microspheres into a composition and expanding the microspheres. An expandable polymeric microsphere includes a polymer shell and a core material in the form of a gas, liquid, or combination thereof. Upon heating to a temperature at or below the melt or flow temperature of the polymeric shell, the polymer shell expands to form the microsphere. Suitable core materials include propane, butane, pentane, isobutane, neopentane, isopentane, and combinations thereof. The thermoplastic resin used for the polymer microsphere shell can influence the mechanical properties of the foam, and the properties of the foam may be adjusted by the choice of microsphere, or by using mixtures of different types of microspheres. Examples of commercially available expandable microspheres include those available under the trade designation EXPANCEL, from Akzo Nobel Pulp and Performance Chemicals AB, Sundsvall, Sweden. Methods of making foams containing expandable polymeric microspheres and particulars of these microspheres are described in U.S. Pat. No. 6,103,152 (Gehlsen et al.).

Foams may also be prepared by forming gas voids in a composition using a variety of mechanisms including, for example, mechanical mechanisms, chemical mechanisms, and combinations thereof. Useful mechanical foaming mechanisms include, for example, agitating (for example, shaking, stirring, or whipping the composition, and combinations thereof), injecting gas into the composition (for example, inserting a nozzle beneath the surface of the composition and blowing gas into the composition), and combinations thereof. Methods of making the foams with voids formed via a foaming agent are described in U.S. Pat. No. 6,586,483 (Kolb et al.). In exemplary embodiments, the foams have a foam density of from 320 kg/m$^3$ to 800 kg/m$^3$. For example, the density can be at least 350, at least 375, at least 400, at least 425, at least 450, at least 475, or at least 500 kg/m$^3$ and up to 800, up to 750, up to 700, up to 650, up to 600 kg/m$^3$.

The skin layers can be adhered to the core to form a three-layered adhesive composition. Any desired thickness of the core and skin layers can be used. In some embodiments, the core is often in a range of 500 micrometers and can be up to 12,000 micrometers or greater. The thickness of often at last 500, at least 600, at least 700, at least 800, at least 1000, at least 1200, at least 1400, at least 1600, at least 1800, or at least 2000 micrometers and up to 12,000, up to 10,000, up to 8000, up to 7000, up to 6000, up to 5000, up to 4000, up to 3000, or up to 2000 micrometers. In some embodiments, each skin layer is often in a range of 25 to 100 micrometers. The thickness can be at least 25, at least 30, at least 35, at least 40, at least 45, at least 50, at least 55, or at least 60 micrometers and up to 100 or greater, up to 95, up to 90, up to 85, up to 80, up to 75, up to 70, up to 65, up to 60, up to 55, or up to 50 micrometers.

EXAMPLES

Unless otherwise noted or readily apparent from the context, all parts, percentages, ratios, etc. in the Examples and the rest of the specification are by weight.

TABLE 1

Materials Used in the Examples

| Abbreviation | Description and Source |
|---|---|
| 3M VHB Tape (4941) | A 1.1 mm thick double-sided acrylic foam tape, obtained from 3M, St. Paul, MN |
| EA | Ethyl acetate, obtained from Sigma Aldrich, St. Louis, MO, USA |
| PETMP | Pentaerythritol tetrakis(3-mercaptopropionate), obtained from Sigma Aldrich, St. Louis, MO, USA |
| AAA | Allyl acetoacetate, obtained from Sigma Aldrich, St. Louis, MO, USA |
| IRGACURE 651 | 2,2'-dimethoxy-2-phenylacetophenone, obtained from Sigma Aldrich, St. Louis, MO, USA |
| Copper substrates | Adhesion test coupons (Dimensions: 4.0" × 1.0" × .0647"), obtained from Joseph T. Ryerson and Son Inc., Coon Rapids, MN |
| MPTMS | 3-mercaptopropyltrimethoxysilane, obtained from Gelest, Morrisville, PA, USA |

90° Peel Test Method

90° Peel Test Panel Surface Preparation

Copper test panels were cleaned with isopropyl alcohol-soaked paper towels to remove contaminants on the surface and were thoroughly dried. Control panels were used without further treatment. Primed panels were prepared by applying primer compositions. Typical concentrations of primer compositions were 5 wt. % in ethyl acetate. Sponge swabs were used to apply primer compositions on target substrates. After primer application, solvent was quickly evaporated without heating.

90° Peel Test Coupon Preparation

A 12.5 mm (0.5 inch) wide strip of double-sided pressure sensitive adhesive 3M VHB tape was first laminated onto a copper test panel having a thickness of 1.1 mm using a 2.0 kg rubber roller to give a bonded article. Then the other side of the foam tape was attached to a 0.13 mm thick anodized aluminum foil by applying 2.0 kg rubber roller to give a final bonded article for 90° peel tests.

Measurement of 90° Peel

After a dwell time of 72 hours at 23° C. and 50% RH, 90° peel test was performed using a Instron 3400 (manufactured by INSTRON, Inc., Norwood, MA) at 30.5 cm/min. (12 in./min), with data collected and averaged over 10 seconds, according to the test method ASTM Designation D3330/D3330M-04. The mode of failure was noted and recorded using the following designations: CS: cohesive split; and CP: clean peel.

Aged samples were tested with the same methods but instead of dwelling 72 hours at 23° C., the bonded article was aged for 14 days at 120° F., 80% RH in a forced air oven before peel adhesion was evaluated.

Example Preparation

Primer A

In a 100 mL round bottom flask, place 4.073 g of allyl acetoacetate, 7.000 g of pentaerythritol tetrakis(3-mercaptopropionate), 0.222 g of Irgacure 651, and 11.073 g of ethyl acetate. The mixture was stirred until it became a homogeneous solution then was UV irradiated with two black UV light bulbs (Philips TL-D 15 W, BLB). The mixture was continuously stirred during the UV irradiation for at least 30 minutes to complete the reaction. The resulting product was a clear transparent liquid. The reaction was confirmed by NMR spectroscopy

TABLE 2

| 90° Peel Test with 72 hours of dwell time under 23 °C and 50% RH | | | | | | |
|---|---|---|---|---|---|---|
| | Primer | Sample # | Average Load (lbf) | Failure mode | Mean (lbf) | Standard Dev. |
| Control A | None | 1 | 14.64 | CP | 14.09 | 0.50 |
| | | 2 | 13.65 | CP | | |
| | | 3 | 13.98 | CP | | |
| Control B | 3-MPTMS | 1 | 8.06 | CP | 9.05 | 0.90 |
| | | 2 | 9.81 | CP | | |
| | | 3 | 9.30 | CP | | |
| EX 1 | Primer A | 1 | 13.87 | CP | 13.63 | 0.38 |
| | | 2 | 13.19 | CP | | |
| | | 3 | 13.84 | CP | | |

TABLE 3

| 90° Peel Test with 14 days of dwell time under 48.9 °C and 80% RH | | | | | | |
|---|---|---|---|---|---|---|
| | Primer | Sample # | Average Load (lbf) | Failure mode | Mean (lbf) | Standard Dev. |
| Control C | None | 1 | 4.77 | CP | 3.61 | 1.10 |
| | | 2 | 2.58 | CP | | |
| | | 3 | 3.48 | CP | | |
| Control D | 3-MPTMS | 1 | 4.65 | CP | 4.51 | 0.59 |
| | | 2 | 3.86 | CP | | |
| | | 3 | 5.01 | CP | | |
| EX 2 | Primer A | 1 | 12.84 | CS | 13.80 | 0.85 |
| | | 2 | 14.46 | CS | | |
| | | 3 | 14.11 | CS | | |

What is claimed is:

1. A primer compound comprising at least one thiol group and at least one diketone group, wherein the primer compound is free of an oxirane group, wherein the primer compound is a reaction product of a mixture free of an oxirane-containing compound, the mixture comprising:

(a) a first compound having at least two thiol groups; and (b) a second compound comprising an ethylenically unsaturated group and a diketone group of formula $—(C{=}O)—CH_2—(C{=}O)—$, wherein the first compound is selected from the group consisting of Formula (III)

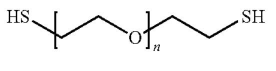
(III)

wherein n is an integer in a range of 1 to 10; Formula (IV)

(IV)
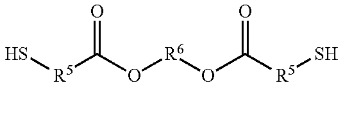

wherein $R^5$ is an alkylene having 1 to 4 carbon atoms; and $R^6$ is an alkylene having 1 to 6 carbon atoms; and Formula (V)

$$C(CH_3)—[CH_2—(C_3H_6—O)_y—O—CH_2—CH(OH)—CH_2—SH]_3 \quad (V)$$

wherein y is equal to 1 or 2.

2. The primer compound of claim 1, wherein the second compound is of Formula (VI)

$$H_3C—(C{=}O)—CH_2—(C{=}O)—O[—CH_2CH_2—O]_x—CH_2CH{=}CH_2 \quad (VI)$$

wherein x is an integer in a range of 0 to 5.

3. An article comprising a first metal-containing substrate and a first surface of a first primer layer positioned adjacent to the first metal-containing substrate, the first primer layer comprising a first primer compound of claim 1, the first primer compound being chelated to a metal in the first metal-containing substrate.

4. The article of claim 3, wherein the article further comprises a first adhesive layer positioned adjacent to a second surface of the first primer layer opposite the first surface of the first primer layer.

5. The article of claim 4, further comprising a second primer layer adjacent to the first adhesive layer opposite the first primer layer, the second primer layer comprising a second primer compound of claim 1; and a second metal-containing substrate positioned adjacent to the second primer layer opposite the first adhesive layer, the second primer compound being chelated to the second metal-containing substrate.

6. The article of claim 4, wherein the article further comprises a foam layer bonded to the first adhesive layer opposite the first primer layer and a second adhesive layer bonded to the foam layer opposite the first adhesive layer.

7. The article of claim 6, further comprising a second primer layer adjacent to the second adhesive layer opposite the foam layer, the second primer layer comprising a second primer compound of claim 1; and a second metal-containing substrate positioned adjacent to the second primer layer opposite the second adhesive layer, the second primer compound being chelated to the second metal-containing substrate.

8. The article of claim 4, further comprising a second substrate that is a second metal-containing substate or a non-metallic substate, the second substrate positioned adjacent to the first adhesive layer opposite the first primer layer.

9. A primer compound comprising at least one thiol group and at least one diketone group, wherein the primer compound is free of an oxirane group, wherein the primer compound is a reaction product of a mixture free of an oxirane-containing compound, the mixture comprising:

(a) a first compound having at least two thiol groups; and (b) a second compound comprising an ethylenically unsaturated group and a diketone group of formula $—(C{=}O)—CH_2—(C{=}O)—$, wherein the second compound is of Formula (VII)

$$H_3C—(C{=}O)—CH_2—(C{=}O)—R^7—CH—CH_2 \quad (VII)$$

wherein $R^7$ is an alkylene having 2 to 6 carbon atoms.

10. A primer compound comprising at least one thiol group and at least one diketone group, wherein the primer compound is free of an oxirane group, wherein the primer compound is a reaction product of a mixture free of an oxirane-containing compound, the mixture comprising:

(a) a first compound having at least two thiol groups; and (b) a second compound comprising an ethylenically unsaturated group and a diketone group of formula $-(C{=}O)-CH_2-(C{=}O)-$, wherein the second compound is of Formula (VIII)

$$H_3C-(C{=}O)-CH_2-(C-O)-O-R^8-O-(C{=}O)-CR^1-CH_2 \quad \text{(VIII)}$$

wherein $R^8$ is an alkylene having 2 to 6 carbon atoms and $R^1$ is hydrogen or methyl.

* * * * *